United States Patent [19]

Nishiwaki et al.

[11] Patent Number: 5,075,667

[45] Date of Patent: Dec. 24, 1991

[54] HUMIDITY SENSOR AND METHOD FOR PRODUCING THE SAME

[75] Inventors: Satoru Nishiwaki, Tokyo; Hiroshi Miyazaki, Yokohama; Koji Murakami, Yokohama; Yukinobu Takahashi, Yokohama, all of Japan

[73] Assignee: Kabushiki Kaisha Toshiba, Kawasaki, Japan

[21] Appl. No.: 443,362

[22] Filed: Nov. 30, 1989

[30] Foreign Application Priority Data

Nov. 30, 1988 [JP] Japan ................. 63-303675

[51] Int. Cl.$^5$ ............................................. H01C 7/00
[52] U.S. Cl. ................................................. 338/35
[58] Field of Search .............. 338/35, 34; 73/335, 73/29.01, 29.02, 29.05, 336.5; 427/101, 102, 103

[56] References Cited

U.S. PATENT DOCUMENTS

| | | | |
|---|---|---|---|
| 4,143,177 | 3/1979 | Kovac et al. | 73/336.5 |
| 4,203,087 | 5/1980 | Kovac et al. | 338/35 |
| 4,482,581 | 11/1984 | Lorin et al. | 338/35 X |
| 4,638,346 | 1/1987 | Inami et al. | 338/35 X |
| 4,642,601 | 2/1987 | Sugawara et al. | 338/35 |
| 4,677,416 | 6/1987 | Nishimoto et al. | 338/35 |
| 4,928,513 | 5/1990 | Sugihara et al. | 338/35 X |

FOREIGN PATENT DOCUMENTS 57-3905  1/1982  Japan.
60-239657 11/1985  Japan.

Primary Examiner—Marvin M. Lateef
Attorney, Agent, or Firm—Foley & Lardner

[57] ABSTRACT

A humidity sensor and a method for producing the same, in which an insulating film is first formed on a substrate. A first sensing film is formed on a first electrode to be separated by a space from the insulating film. A second sensing film of the same material as the first sensing film is again formed on the first sensing film and the insulating film, the space therebetween being filled with the second sensing film. Thus a uniform surface etching of the second sensing film is effected, to obtain a continuous flat film layer composed of the sensing film and the insulating film with a continuous flat surface, and in which a second electrode is formed on at least the sensing film.

11 Claims, 6 Drawing Sheets

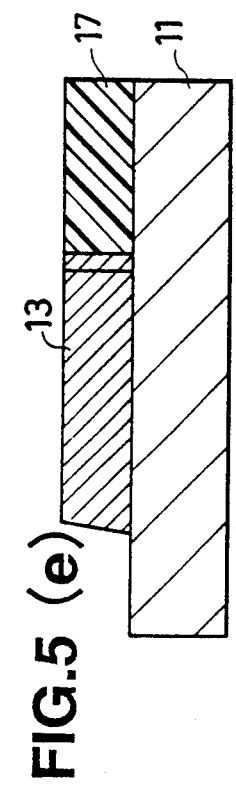
FIG.5 (a)
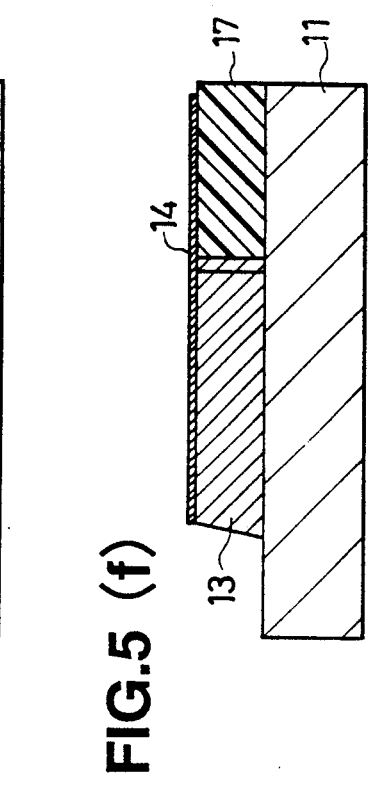
FIG.5 (b)
FIG.5 (c)
FIG.5 (d)
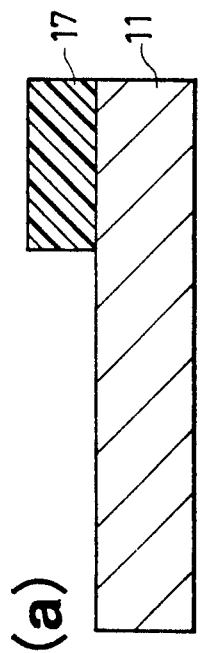
FIG.5 (e)
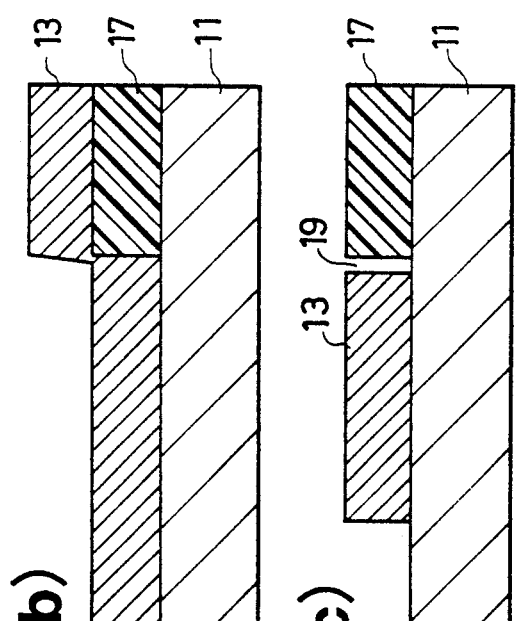
FIG.5 (f)
FIG.5 (g)
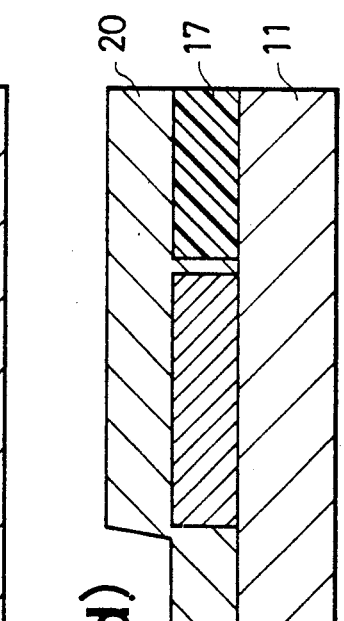
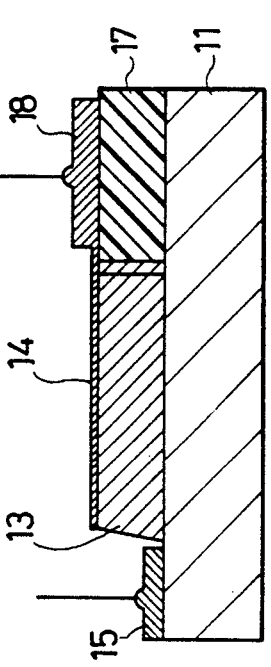

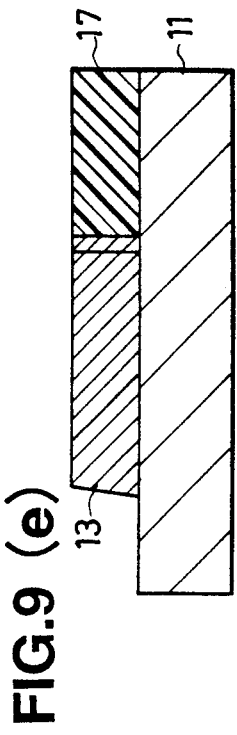
FIG.9 (e)
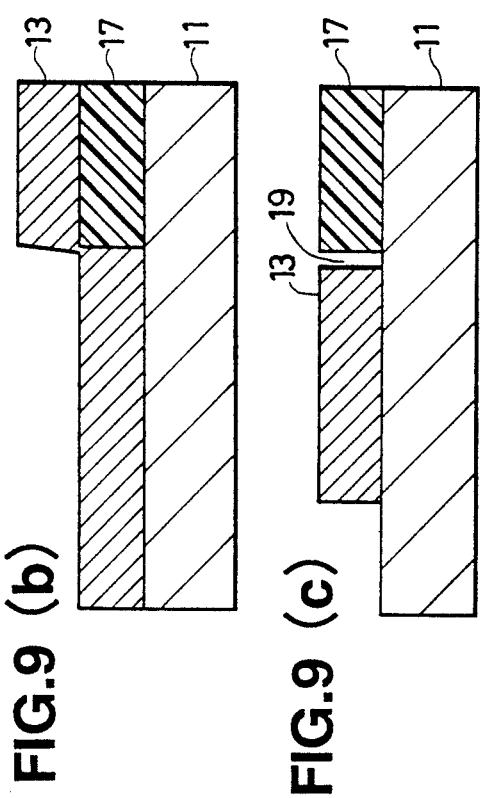
FIG.9 (f)
FIG.9 (g)
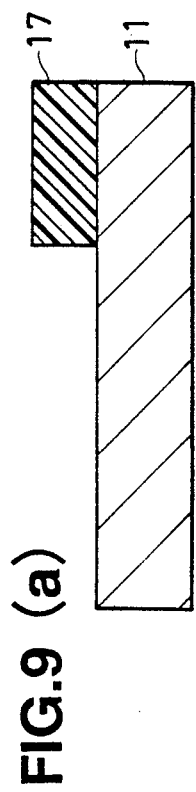
FIG.9 (a)
FIG.9 (b)
FIG.9 (c)
FIG.9 (d)

HUMIDITY SENSOR AND METHOD FOR PRODUCING THE SAME

BACKGROUND OF THE INVENTION

1. Field of the Invention

The present invention relates to a humidity sensor for use in an air conditioning system or the like, and a method for producing the humidity sensor.

2. Description of the Background Art

A variety of humidity sensors have been developed. The usual sensing principles of humidity sensing in which they operate are:

(1) Conductivity variation due to adsorption of water to porous ceramics is utilized.

(2) Dielectric constant variation or conductivity variation due by adsorption of water to high polymers;

(3) Ion conductivity variation of an electrolyte; and (4) Thermal conductivity of a sensing material.

In such humidity sensors, an electric property change with respect to humidity variation in the atmosphere is utilized, that is, the humidity variation is detected in terms of an electric signal having a different value.

In FIG. 1, there is shown a conventional humidity sensor comprising a substrate 1, a lower electrode 2 formed on the substrate 1, a sensing film 3 formed on the lower electrode 2 and an upper electrode 4 formed on the sensing film 3, which are successively laminated one on another. One end of the upper electrode 4 is extended down onto the substrate 1, and a bonding pad 5 is connected to the extended upper electrode 4 on the substrate 1 for coupling to an external circuit (not shown).

In this case, the sensing film 3 usually detects the humidity in the atmosphere through the upper electrode 4, and the upper electrode 4 is made thin in so as to promote the permeation of the humidity. The sensing film 3 is approximately several thousands Å to several μm in thickness in order to have a humidity sensing ability with a sufficient capacity. Hence, the upper electrode 4 is formed in a stair shape to reach the bonding pad 5. In the thin upper electrode 4, a crack is apt to take place in its side wall portion 4a, and thus disconnection may be caused by the crack.

In FIG. 2, there is shown another conventional humidity sensor having basically the same structure as that of the aforementioned conventional humidity sensor shown in FIG. 1. In this case, a thin upper electrode 4 is provided with a vertical electrode 6 for reinforcing the step portion thereof, i.e., the side wall portion and the adjacent end portion of the upper main flat portion. The vertical electrode 6 is formed sufficiently thick by the vapor deposition method or the like, and the crack in the side wall portion can be effectively prevented.

However, in this sensor, the humidity sensing property of the sensing film 3 is liable to be deteriorated by heat. The vertical electrode 6 is formed so as to have the same or greater thickness as or than that of the sensing film 3. This is carried out for a long period of time in a high temperature step, which can readily cause the deterioration of the humidity sensing property of the sensing film 3.

In FIG. 3, there is shown still another conventional humidity sensor, in which a pair of lower electrodes 2a and 2b, separated from each other, are provided on a substrate 1. Then, a sensing film 3 and an upper electrode 4 are consecutively formed on the lower electrodes 2a and 2b formed on the substrate 1. A pair of bonding pads 5a and 5b for coupling with an external circuit are attached to the opposite end portions of the lower electrodes 2a and 2b.

In this case, no side wall or no vertical electrode of the above described conventional humidity sensors is required, but there is a series of two capacitors formed between the upper electrode 4 and the two lower electrodes 2a and 2b, the sensing film 3 being interposed therebetween. A capacity variation of the sensing film 3 is picked up. The detecting efficiency of the sensing film 3 having the same area as the above described conventional humidity sensors is fairly reduced. (For instance, the capacity is reduced to one fourth, because of a series of two capacitors).

In conventional humidity sensors, as described above, high detecting efficiency, prevention of a crack in the step portion of the upper electrode and the high reliability of the detection, cannot be attained at the same time.

SUMMARY OF THE INVENTION

Accordingly, it is an object of the present invention to provide a humidity sensor, free from these defects and disadvantages of the prior art, which is capable of providing a high humidity sensing ability and reliability, and preventing occurrences of cracks in a side wall portion of an upper electrode.

It is another object of the present invention to provide a method for producing a humidity sensor free from the aforementioned defects and disadvantages of the prior art, which sensor is capable of preventing, deterioration of the sensing property of a sensing film, and providing a high humidity sensing ability and a high sensing reliability.

In accordance with one aspect of the present invention, there is provided a humidity sensor, comprising a sensing film formed on a first electrode, an insulating film formed on a substrate to continuously connect to the sensing film, the sensing film and the insulating film constituting a continuous flat film layer with a continuous flat surface, and a second electrode formed on at least the sensing film.

In accordance with another aspect of the present invention, there is provided a method for producing a humidity sensor, comprising the steps of forming an insulating film on a substrate having a first electrode in a surface portion thereof, forming a sensing film on the first electrode to be separated by a space from the insulating film of the substrate, forming the sensing film over the previously formed sensing film and the insulating film while the space between the previously formed sensing film and the insulating film is filled up with the sensing film, effecting a uniform surface etching of the sensing film until at least the insulating film is exposed, to obtain a continuous flat film layer composed of the sensing film and the insulating film with a continuous flat surface, and forming a second electrode on at least the sensing film.

BRIEF DESCRIPTION OF THE DRAWINGS

These and other objects, features and advantages of the present invention will more fully appear from the following description of the preferred embodiments with reference to the accompanying drawings, in which:

FIGS. 5a to 5g illustrate a process for producing the humidity sensor shown in FIG. 4;

FIGS. 9a to 9g illustrate a process for producing the humidity sensor shown in FIG. 8.

DESCRIPTION OF THE PREFERRED EMBODIMENTS

Figure 1:
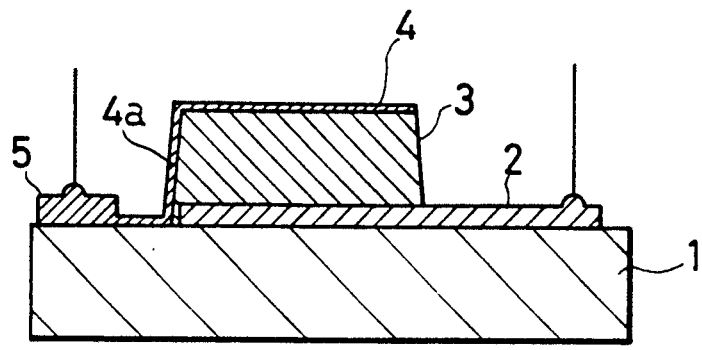
FIGS. 1 to 3 are longitudinal cross sections of conventional humidity sensors.
Figure 2:
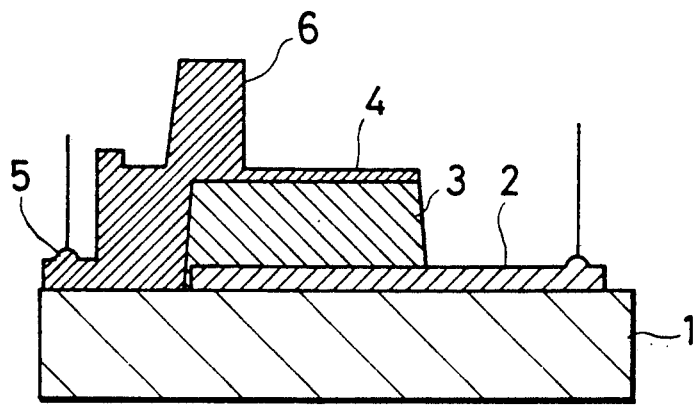
Figure 3:
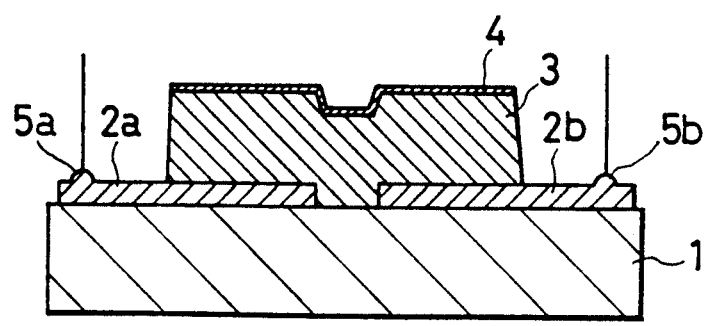
Figure 4:
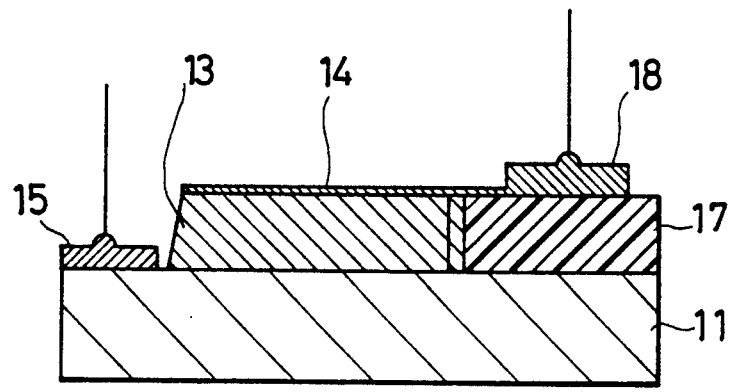
FIG. 4 is a longitudinal cross section of a first embodiment of a humidity sensor according to the present invention.

Referring now to the drawings, wherein like reference characters designate like or corresponding members throughout the several views and thus the repeated description thereof may be omitted for the brevity, there is shown in FIG. 4 the first embodiment of a humidity sensor according to the present invention.

As shown in FIG. 4, a humidity sensing film 13 composed of a polyimide film and an adjacent insulating film 17 composed of an silicon oxide film having a thickness of approximately 1 to 2 $\mu$m are formed on an N-type silicon substrate 11, serving also as a lower electrode, in which an impurity is doped and which has a resistivity of approximately several $\Omega$cm. An upper electrode 14 composed of an air-permeable metallic thin film is formed over the entire upper surface of the sensing film 13 and a partial upper surface of the insulating film 17, thereby obtaining a humidity sensing unit. Two bonding pads 15 and 18 are formed on the opposite side end portions of the substrate 11 and the upper electrode 14 for coupling the humidity sensing unit to an external circuit (not shown).

Then, a process for producing the humidity sensor described above will now be described in connection with FIG. 5.

In FIG. 5a, an silicon oxide film having a thickness of approximately 1 to 2 $\mu$m is formed on the surface of the N-type silicon substrate 11 by using a thermal oxidation method or a CVD method, and then a pattern etching of the silicon oxide film is carried out by using a usual photolithographic method to obtain an insulating film 17 on the substrate 11.

In FIG. 5b, a polyimide film 13 having approximately 1 to 2 $\mu$m is formed over the entire surface of the substrate 11 and the insulating film 17 formed thereon by using a spin coat method, and the surface is flattened so that the thickness of the polyimide film 13 may be approximately the same as that of the insulating film 17.

In FIG. 5c, after curing the polyimide film 13 formed on the insulating film 17 and substrate 11 altogether at approximately 150° to 300° C. for approximately 30 minutes, a pattern etching of at least a part of the polyimide film 13 by using the photolithographic method so that a gap 19 having a length of approximately the same or less as the thickness of the insulating film 17 is formed between the insulating film 17 and the remained polyimide film 13 as the humidity sensing film. That is, in this step, the polyimide film 13 as the humidity sensing film is formed on the substrate 11 to be separated by a certain space 19 from the insulating film 17 on the substrate 11.

In FIG. 5d, a polyimide film 20 having a thickness of approximately 1 to 2 $\mu$m is formed again over the entire surface of the polyimide film 13, the insulating film 17 and the substrate 11 supporting the polyimide film 13 and insulating film 17 while the gap 19 between the polyimide film 13 and the insulating film 17 is completely filled up with the polyimide film 20, and the surface is flattened so that the thickness of the polyimide film 20 may be approximately 1 $\mu$m, and the surfaces of the previously formed polyimide film 13 and the insulating film 17 may be flat.

In FIG. 5e, after curing the polyimide film 20 formed on the entire surface of the polyimide film 13 and the insulating film 17 on the substrate 11 altogether at approximately 150° to 300° C. for approximately 30 minutes, a uniform surface etching of the polyimide film 20 is effected by using a reactive ion etching (RIE) method until the insulating film 17 is exposed so that the exposed insulating film 17 and polyimide film 13 may be continuously linked with a continuous integrated flat surface therebetween. In this step, when some residues such as the polyimide film or the like remain on the surface of the insulating film 17, they can be removed by combining a wet etching method with the RIE method.

In FIG. 5f, after curing the polyimide film 13 and insulating film 17 formed on the substrate 11 altogether at approximately 150° to 300° C. for approximately 1 hour, an air-permeable thin film of a precious metal such as gold, chromium or the like, having a thickness of approximately several hundreds Å is formed over the surface of the polyimide film 13 and the insulating film 17 by using a sputtering method or a vapor deposition method, and a pattern etching of the air-permeable thin film is effected by the photolithographic method to obtain an upper electrode 14 on the polyimide film 13 and the insulating film 17, thereby obtaining a humidity sensing unit.

In FIG. 5g, a thick film of the same material as the upper electrode 14, having a thickness of approximately 1 $\mu$m is formed on the opposite ends of the substrate 11 and the upper electrode 14 by using the sputtering method or the vapor deposition method, and then a pattern etching of the thick film is carried out by using the photolithographic method to obtain bonding pads 15 and 18 on the end portions of the substrate 11 and the upper electrode 14, thereby obtaining a humidity sensor according to the present invention.

In this embodiment, as described above, on the substrate the polyimide film and the insulating film are continuously connected to each other with a continuous integrated flat surface. The upper electrode is uniformly formed, and extends smoothly in the flat form on the polyimide film and the insulating film without causing any crack. Also, the bonding pad 18 is formed on one end of the upper electrode 14 on the insulating film 17. The humidity sensor of the present invention can be produced without providing the vertical electrode for reinforcing the step portion of the upper electrode of the conventional humidity sensor and without using high temperature steps for a long time, and thus the humidity sensing property of the sensing film can be maintained in good condition without suffering any deterioration.

In this case, the steps shown in FIGS. 5b to 5e are essential because it is almost impossible to allow the polyimide film 13 to continuously connect with the insulating film 17 with a continuous integrated flat surface by a single step, i.e., from the step shown FIG. 5a directly to the step shown in FIG. 5e. The reasons for this are as follows. In the case that the polyimide film is to be formed adjacent to the insulating film in contact therewith, when a mask pattern positioning by the photolithographic method is shifted and the polyimide film is formed over the insulating film even by a slight amount, an irregularity or unevenness is increasedly caused in the surface of the contact portion between the polyimide film and the insulating film. In turn, when a space is produced even a slight amount between the polyimide film and the insulating film by an incorrect mask pattern positioning using the photolithographic method, a short-circuit may be readily caused between the lower electrode of the substrate and the upper electrode formed on the polyimide film and the insulating film.

In this embodiment, as described above, the polyimide film 13 as the humidity sensing film is formed to be separated by a certain small space 19 from the insulating film 17 on the substrate 11 (see FIGS. 5b and 5c), and then another polyimide film 20 is formed over the polyimide film 13 and the insulating film 17 on the substrate 11 while the small space 19 between the polyimide film 13 and the insulating film 17 is filled up with the polyimide film 20 (see FIG. 5d). Then, the uniform surface etching of the polyimide film 20 is effected by using the RIE method to obtain the continuous flat film layer composed of the polyimide film 13 and the insulating film 17 (the polyimide 20 filling up the gap 19 between the polyimide film 13 and the insulating film 17) with the continuous flat surface, which are continuously connected to each other as described above (see FIG. 5e). Then, the air-permeable upper electrode 14 is readily formed over the continuous flat film composed of the polyimide film and the insulating film (see FIG. 5f).

In this embodiment, the substrate 11 is not restricted to the N-type silicon substrate, and, of course, a P-type silicon substrate can be also used. In this case, it is necessary to select metallic materials capable of readily effecting an ohmic contact with the substrate for the bonding pad. Further, cellulose materials, photosensitive materials, photopolymerizing materials or the like can be also used for the humidity sensing film.

Figure 6:
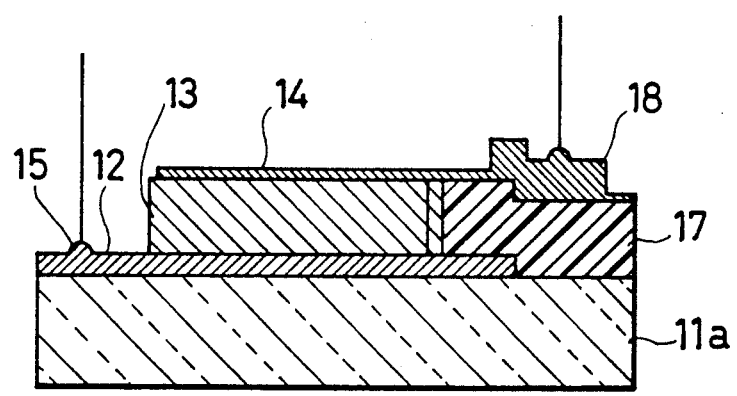
FIG. 6 is a longitudinal cross section of a second embodiment of a humidity sensor according to the present invention.

In FIG. 6, there is shown the second embodiment of the humidity sensor according to the present invention, having the same structure as that of the first embodiment shown in FIG. 4, except that a lower electrode 12 composed of a thin metal film of a precious metal, such as gold, is formed on an insulating glass substrate 11a.

Figure 7:
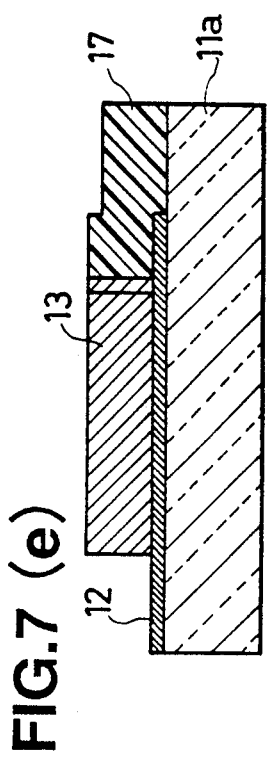
FIGS. 7a to 7g illustrate a process for producing the humidity sensor shown in FIG. 6.
Figure 7:
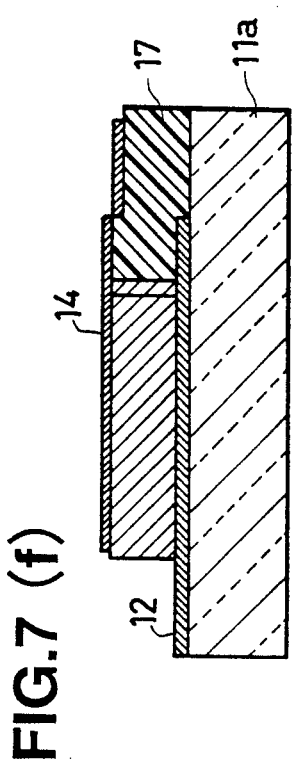
Figure 7:
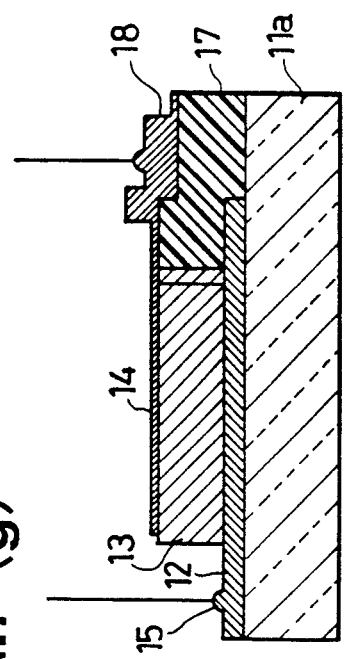
Figure 7:
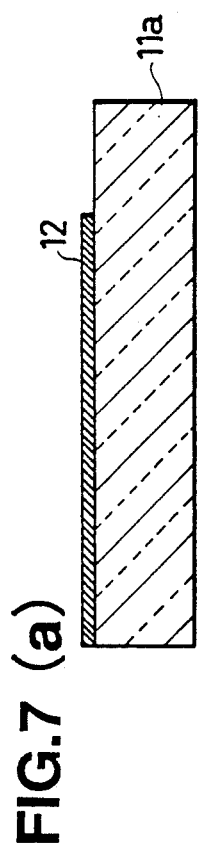
Figure 7:
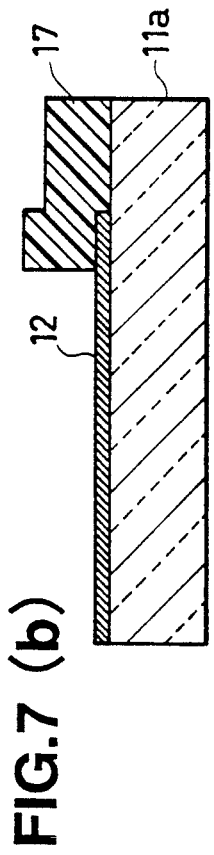
Figure 7:
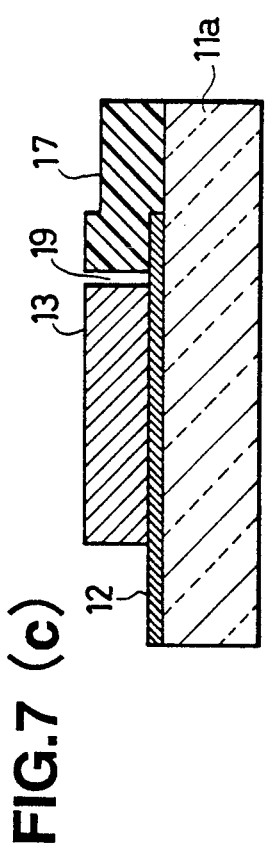
Figure 7:
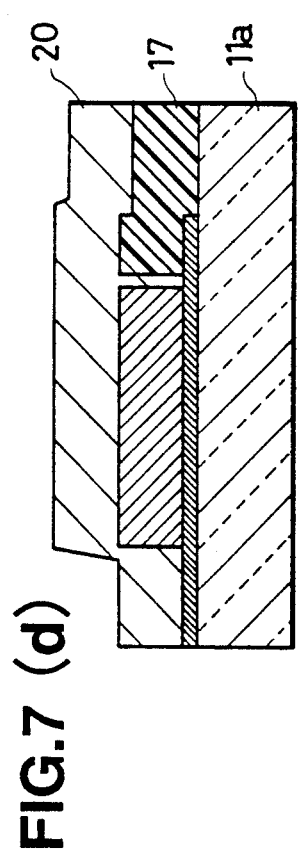

In FIG. 7, there is shown a method for producing the humidity sensor shown in FIG. 6. In this method, firstly, a thin metal film of a precious metal, such as gold, having a thickness of approximately several thousands Å to several μm, is formed on the surface of an insulating glass substrate 11a by using the vapor deposition method, and then a pattern etching of the metal thin film is effected by using the photolithographic method to obtain an lower electrode 12, as shown in FIG. 7a. Then, as shown in FIG. 7b, an insulating film 17 having a thickness of approximately 1 to 2 μm is formed on the substrate 11a and the lower electrode 12 formed thereon in a conventional manner. In FIGS. 7c to 7g, polyimide films 13 and 20 as a humidity sensing film, an upper electrode 14 and bonding pads 15 and 18 are formed on the substrate 11a in the same manner as those of the first embodiment shown in FIGS. 5b to 5g, thereby obtaining a humidity sensor according to the present invention.

In this embodiment, although the glass plate is used as the substrate 11a, however, other insulating plate materials may be used. The same effects and advantages as those of the first embodiment described above can be, of course, obtained.

Figure 8:
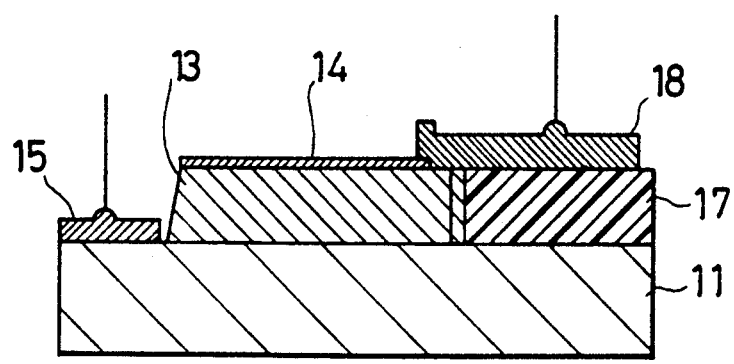
FIG. 8 is a longitudinal cross section of a third embodiment of a humidity sensor according to the present invention.

In FIG. 8, there is shown the third embodiment of the humidity sensor according to the present invention, having the same construction as that of the first embodiment shown in FIG. 4, except that an upper electrode 14 is formed on only a polyimide film 13, and a bonding pad 18 is formed over an insulating film 17 and one end portion of the upper electrode 14. This embodiment is intended to overcome a bad contact property of an upper electrode 14 with an insulating film 17. That is, when the contact property of the upper electrode 14 with the insulating film 17 is not good, the upper electrode 14 formed on the insulating film 17, as described in the first and second embodiments, is liable to peel off the insulating film 17 during the operation of the humidity sensor. In order to prevent this problem, the upper electrode 14 is formed on only the polyimide film 13, and then the bonding pad 18 capable of performing a tight contact with both the upper electrode 14 and the insulating film 17 is formed over the insulating film 17 and one end of the upper electrode 14.

In FIG. 9, there is shown a method for producing the humidity sensor shown in FIG. 8. In this method, the steps shown in FIGS. 9a to 9e are the same as those of the first embodiment as shown in FIGS. 5a to 5e.

Then, in FIG. 9f, an upper electrode 14 is formed on the entire surface of the continuous film layer of the polyimide film 13 and the insulating film 17 in the same manner as the first embodiment, and then a pattern etching of the upper electrode 14 is carried out by using the photolithographic method in order to leave the upper electrode 14 only on the polyimide film 13.

In FIG. 9g, metals such as titanium and gold are consecutively formed on the insulating film 17 and the upper electrode 14. Being approximately several thousands Å in thickness, each metal forms a bonding pad 18. Then, a pattern etching of the bonding pad 18 by using a metal mask, is effected so that the bonding pad 18 may be laid over the insulating film 17 and one end tip of the upper electrode 14, thereby obtaining a humidity sensor according to the present invention. The same effects and advantages as those of the first embodiment can be obtained.

In these embodiments described above, the sputtering method may be replaced by the vapor deposition method, and the patterning of the upper electrode may be carried out by the metal mask method instead of the photolithographic method. Also, the patterning of the silicon oxide film and the humidity sensing film may be performed by a dry etching method such as a CDE method instead of the wet etching method.

Further, in order to improve the contact property among the substrate, the humidity sensing film, the insulating film and the lower and upper electrodes, some pretreatment may be effected. For instance, when the gold thin film is to be formed on the silicon oxide film formed on the substrate, a titanium or chromium thin film may be formed as an anchor prior to the formation of the gold thin film.

Figure 10:
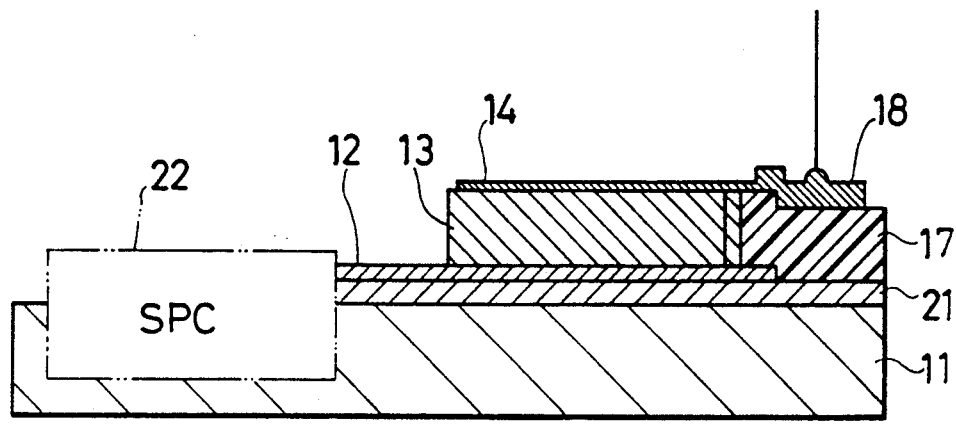
FIGS. 10 and 11 show fourth and fifth embodiments of a humidity sensor according to the present invention.

In FIG. 10, there is shown the fourth embodiment of the humidity sensor according to the present invention, having a similar structure to that of the first embodiment shown in FIG. 4. In this embodiment, a silicon oxide film 21 is formed on the entire surface of an N-type silicon substrate 11 in order to separate the substrate 11 from a humidity sensor unit to be formed on the silicon oxide film 21 of the substrate 11, the humidity sensor unit being formed in the same manner as the second embodiment shown in FIG. 6. In this case, the lower electrode 12 is formed on the silicon oxide film 21 to extend to and connect with a signal processing circuit (SPC) 22 provided on the substrate 11 apart from the humidity sensor unit without requiring a bonding pad for connecting the lower electrode 12 to the signal processing circuit 22.

Figure 11:
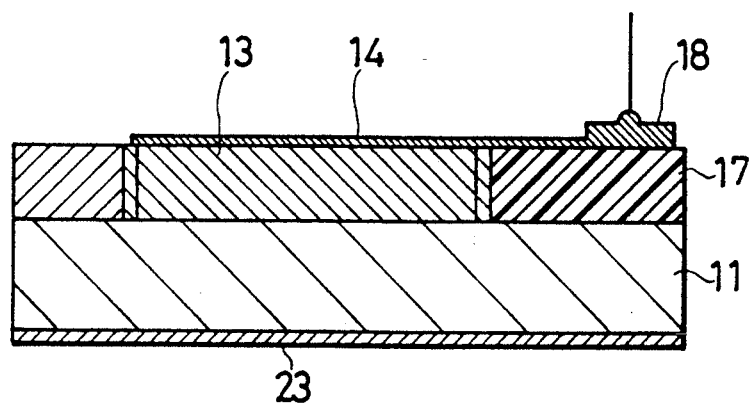

In FIG. 11, there is shown the fifth embodiment of the humidity sensor according to the present invention, having the same structure as that of the first embodiment shown in FIG. 4, except that a gold thin film 23 is formed on the back surface of the substrate 11 by using the vapor deposition method for connecting the lower electrode of the N-type silicon substrate 11 to an external circuit. This substrate having the gold thin film 23 on the back surface may be mounted to a metal plate.

As described above, according to the present invention, a first humidity sensing film is formed on a lower electrode to be separated by a certain space from an insulating film, and then a second humidity sensing film of the same material as the first humidity sensing film is again formed over the entire surface of the first sensing film and the insulating film while the space therebetween is filled up with the second humidity sensing film. Then, a uniform surface etching of the second humidity sensing film is effected to obtain a continuous flat film layer composed of the humidity sensing film and the insulating film with the continuous flat surface.

Therefore, the upper electrode is uniformly formed and smoothly extends in the flat form on the sensing film and the insulating film without causing an irregularity or unevenness in the surface of the contact portion between the sensing film and the insulating film due to the remained sensing film on the insulating film and causing a short-circuit between the lower and upper electrodes due to the space between the sensing film and the insulating film. The humidity sensor of the present invention can be produced without providing the vertical electrode for reinforcing the step portion of the upper electrode of the conventional humidity sensor and without using a high temperature steps for a long time, and thus the humidity sensing property of the sensing film can be maintained in the good conditions without suffering any deterioration.

Although the present invention has been described in its preferred embodiments with reference to the accompanying drawings, it it readily understood that the present invention is not restricted to the preferred embodiments and that various changes and modifications can be made by those skilled in the art without departing from the spirit and scope of the present invention.

What is claimed is:

1. A humidity sensor comprising:
    a substrate having an upper surface functioning as a first electrode;
    a humidity sensing film formed on said first electrode;
    an insulating film formed on said substrate and located adjacent to said sensing film;
    a second electrode coated on and extending over said sensing film and said insulating film; and
    a bonding pad provided on said insulating film and electrically connected with said second electrode, wherein said sensing film and said insulating film have upper surfaces flush with each other and said second electrode extends over said sensing film and said insulating film without a step.

2. The sensor of claim 1, wherein the first electrode is a silicon substrate.

3. The sensor of claim 1, wherein the first electrode is a thin metal film formed on an insulating substrate.

4. The sensor of claim 1, wherein first and second boding pads are formed on end portion of the first and second electrodes, respectively.

5. The sensor of claim 1, wherein a first bonding pad is formed on the first electrode, and a second bonding pad is formed on the insulating film and one end of the second electrode formed on only the sensing film.

6. The sensor of claim 2, wherein a thin metal film is formed on a surface of the substrate.

7. A method of forming humidity sensors comprising:
    forming an insulating film on a substrate having an upper surface functioning as a first electrode;
    forming a sensing film, made of a humidity sensitive material, on said substrate in order that said insulating film and said sensing film are located adjacent each other on said substrate and separated by a gap therebetween;
    coating said humidity sensitive material over said insulating film and said sensing film in order to fill up said gap with said humidity sensitive material;
    etching back said humidity sensitive material to make the upper surfaces of said sensing film and said insulating film flush with each other, so that the upper surfaces of said sensing film and said insulating film form a flat continuous surface; and
    forming a second electrode on the upper surfaces of said sensing film and said insulating film with a bonding pad in which said second electrode terminates on said insulating film.

8. The method of claim 7, also including the step of forming first and second bonding pads on end portions of the first and second electrodes, respectively.

9. The method of claim 7, also including the step of forming a first bonding pad on the first electrode and a second bonding pad on the insulating film and one end of the second electrode formed on only the sensing film.

10. The method of claim 7, wherein uniform surface etching is carried out by using a reactive ion etching method.

11. The method of claim 7, also including the step of forming a thin metal film on a surface of the substrate.

* * * * *